United States Patent [19]

Nannelli et al.

[11] 4,082,793
[45] Apr. 4, 1978

[54] AROMATIC PHOSPHINIC ACIDS CONTAINING SULFONE LINKAGE

[75] Inventors: Piero L. Nannelli, King of Prussia; Harold G. Monsimer, East Norriton, both of Pa.

[73] Assignee: The United States of America as represented by the Secretary of the Navy, Washington, D.C.

[21] Appl. No.: 767,095

[22] Filed: Feb. 9, 1977

[51] Int. Cl.² .......................... C07F 9/30; C08G 79/04
[52] U.S. Cl. .............................. 260/502.4 R; 260/2 P; 260/551 P; 260/607 A
[58] Field of Search ................................ 260/502.4 R

[56] References Cited

U.S. PATENT DOCUMENTS

| 3,316,332 | 4/1967 | Calhoun et al. | 260/502.4 R |
| 3,705,920 | 12/1972 | Patchett | 260/502.4 R |
| 3,966,486 | 6/1976 | King et al. | 260/502.4 R |

OTHER PUBLICATIONS

Nannelli et al., "Office of Naval Research–Technical Report No. 17", Feb., 1976.

Primary Examiner—Joseph E. Evans
Attorney, Agent, or Firm—R. S. Sciascia; A. L. Branning; R. D. Johnson

[57] ABSTRACT

Phosphinic acids of the formula

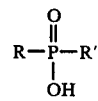

wherein
(A) R is

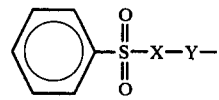

(1) X is 3-phenylene or 4-phenylene, and
(2) Y is a direct bond,

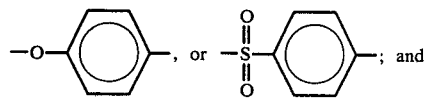

(B) R' is R, lower alkyl of from 1 to 3 carbon atoms, 4-biphenylyl, or phenyl. These acids are neutralized with an equivalent amount of alkali metal carbonates to form alkali metal salts which react with ZnCl₂ to form polymers having high thermal stability.

68 Claims, No Drawings

AROMATIC PHOSPHINIC ACIDS CONTAINING SULFONE LINKAGE

BACKGROUND OF THE INVENTION

This invention generally relates to phosphinic acids and more particularly to aromatic sulfonyl substitute phosphinic acids.

Polymeric metal dialkyl, diaryl and arylalkyl-phosphinates have been discussed in the literature. For instance, see "polymeric Metal Phosphinates", B. P. Block, Inorg. Macromol. Rev. 1 (1970) 115–125. Of particular interest are the polymers containing tetrahedral zinc (II) centers and symmtrical bridging O,O'-phosphinate groups in polymeric structures, such as

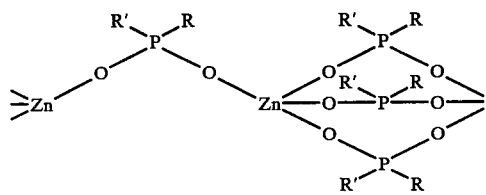

or

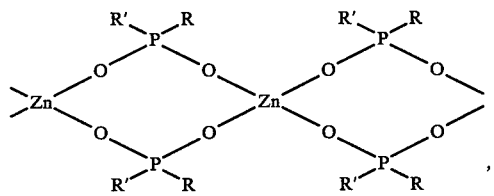

wherein R and R' may be alkyl or aryl groups.

The zinc (II) and phosphinates groups are strong electrostatic centers. Strong electrostatic attraction between centers on adjacent polymer chains gives the dialkyl-, diaryl- and arylalkyl- zinc phosphinate polymers the properties of three dimensional polymers having crosslinkage between chains. As a result, the polymer chains do not easily slide over each other, causing the polymers to form brittle rather than flexible coatings. For instance, the diphenyl- and dimethyl- zinc phosphinate polymers form very brittle coatings. If the aryl and alkyl side groups are large enough to insulate the electrostatic centers on adjacent chains from each other, the polymer coatings will be flexible. For example, zinc phosphinate polymers in which the side groups are alkyl of 8 carbon atoms have a flexibility comparable to polyethylene. Unfortunately, polymers having these large aryl or alkyl side chains have poor thermal stability. The problem is therefore to develop polymers which are both flexible and thermally stable.

In addition to being flexible and thermally stable, the zinc (II) bis(phosphinate) polymers should be melt and/or solution processable. The symmetric diaryl or dialkyl zinc (II) bis(phosphinate) polymers, such as the diphenyl- or dimethyl-, have high energies of crystalization. As a result, these symetric polymers have very high melting points at which they usually decompose rather than melt; they also are insoluble in common solvents.

SUMMARY OF THE INVENTION

Accordingly, one object of this invention is to provide new phosphinic acids and alkali metal salts of these acids.

Yet another object of this invention is to provide new chemical compounds which react with ZnCl$_2$ to produce polymer coatings having high thermal stability.

A further object of this invention is to provide new chemical compounds which react with ZnCl$_2$ to produce polymer coating which resist oxidation at high temperatures.

A still further object of this invention is to provide new chemical compounds which react with ZnCl$_2$ to produce flexible polymer coatings.

Yet another object of this invention is to provide polymers which are melt or solution processable.

These and other objectives of this invention are accomplished by providing phosphinic acids of the formula

wherein
(A) R is

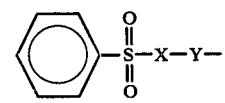

(1) X is selected from the group consisting of 3-phenylene and 4-phenylene, and
(2) Y is selected from the group consisting of a direct bond,

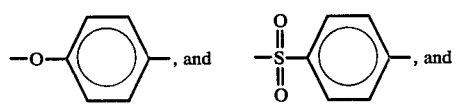

(B) R' is selected from the group consisting of R, lower alkyl of from 1 to 3 carbon atoms, 4-biphenylyl, and phenyl, wherein R is as defined above.

Neutralization of these acids with an equivalence of alkali metal carbonate produces the alkali metal salt of the acid. These alkali metal salts react with zinc (II) chloride to form polymer coatings having high oxidative and thermal stability.

DESCRIPTION OF THE PREFERRED EMBODIMENT

The symmetric phosphinic acids (R' = R) of this invention can be prepared by reacting two moles of RLi with one mole of diethyl dichlorophosphoramide,

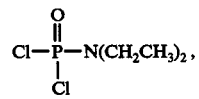

to form a phosphoramide of the formula

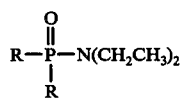

which can then be hydrolyzed to form the phosphinic acid of the formula

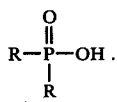

Example 1 illustrates the reaction conditions for this synthesis. Note that the lithium compound, RLi, is formed in solution by the interaction of RBr and butyl lithium. The symmetric phosphinic acid may also be synthesized by reacting two moles of RMgBr with one mole of the diethyl dichlorophosphoramide under standard grignard conditions and then hydrolysing the the resulting phosphoramide to form the acid. A third method of synthesizing these symetric phosphinic acids is to react two moles of diazonium salt, $RN\equiv N^+BF_4^-$, with one mole of the diethyl dichlorophosphoramide, followed by hydrolysis to give the acid. In order to force the addition of two moles of $R-N\equiv N^+BF_4^-$, the reaction conditions will be more rigorous (e.g. higher reaction temperature) than the conditions used in Examples 12, 13, 14, and 15.

The unsymmetric phosphinic acid in which R' is lower alkyl or from 1 to 3 carbon atoms, 4-biphenylyl, or phenyl are synthesized by reacting one mole of the RLi with one mole of one of the following:
  diethyl chloromethylphosphoramide,
  diethyl chloroethylphosphoramide,
  diethyl chloro-n-propylphosphoramide,
  diethyl chloroisopropylphosphoramide,
  diethyl chloro(4-biphenylyl) phosphoramide,
  or diethyl chlorophenylphosphoramide
to form a phosphoramide of the formula

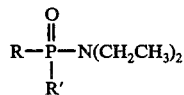

which is then hydrolyzed to form the unsymmetric phosphinic acid of the formula

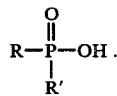

Examples 4 illustrates the reaction conditions for this synthesis. Alternatively, one mole of RMgBr can be used under normal grignard reaction conditions in place of RLi. A third method of synthesizing the unsymmetric phosphinic acids is to react one mole of diazonium salt, $RN\equiv N^+BF_4^-$, with one mole of the chlorophosphoramide to produce the phosphoramide which is hydrolyzed to give the acid.

Examples 12, 13, 14, and 15 illustrate yet another method of synthesizing the unsymmtric phosphinic acids. One mole of diazonium, salt, $RN\equiv N^+BF_4^-$, is reacted with one of the following:
  dichloromethyl phosphine,
  dichloroethyl phosphine,
  dichloro-n-propyl phosphine,
  dichloroisopropyl phosphine,
  dichloro(4-biphenylyl) phosphine, or
  dichlorophenyl phosphine to form a phosphine of the formula

which decomposes when water is added to give the phosphinic acid of the formula

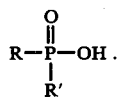

The RLi and $RN\equiv N^+BF_4^-$ are easily synthesized from commercially available materials using conventional reaction steps. For instance, the synthesis of 3-aminophenyl phenyl sulfone and 4-aminophenyl phenyl sulfone are disclosed by M. E. Heppenstall and S. Smiles, J. Chem. Soc. 899 (1938). These amines are converted according to the procedures os Examples 13 and 14 into diazonium salts of the formulas

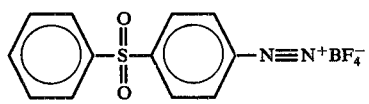

and

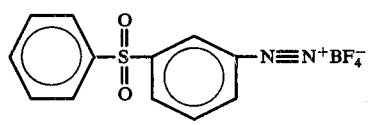

These Diazonium salts can be converted by CuBr in a conventional Sandmeyer reaction to give

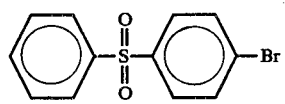

and

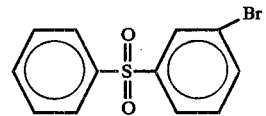

which are converted by butyl lithium to

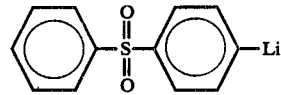

and

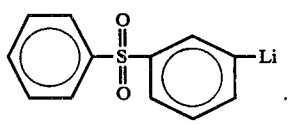

The decomposition of diazonium salts in water is a conventional method of producing pure phenols. Thus, by decomposing the above diazonium salts in water,

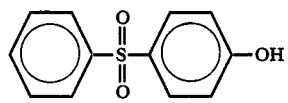

and

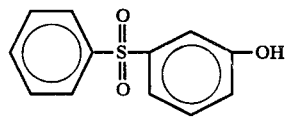

can be produced. These phenols react with dibromobenzene in the presence of copper and base (see example 2) to produce

and

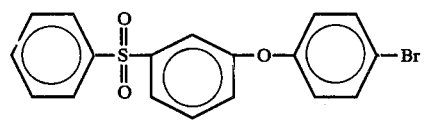

Treatment with butyl lithium replaces the bromine with lithium on these compounds. The sodium salts of the above phenols can be reacted with 4-chloronitrobenzene under the conditions of example 8 to produce nitro compounds. Reduction of the nitro compounds to amines followed by treatment with tetrafluoroboric acid would give

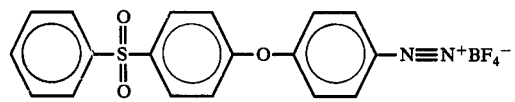

and

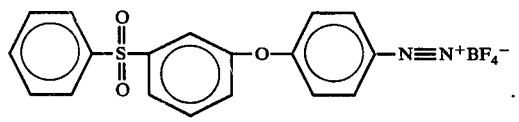

Examples 5 through 11 illustrate the steps for converting

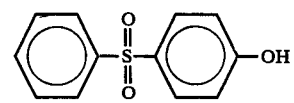

into

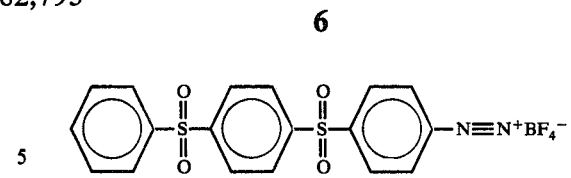

starting with

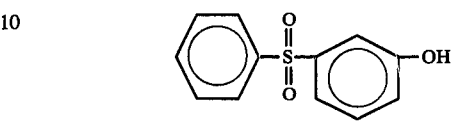

the same procedure can be used to produce

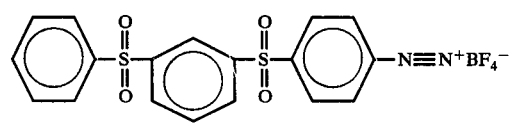

These diazonium salts can be converted by Sandmeyer reaction (CuBr) to the corresponding bromides which will react with butyl lithium to give

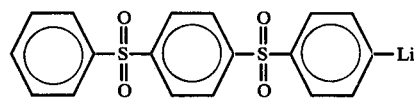

and

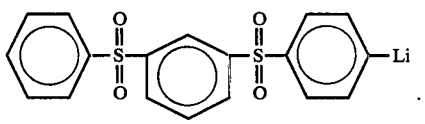

The phosphinic acids of the present invention react with zinc (II) chloride to produce zinc (II) bis(phosphinate) polymers having sulfonyl side groups. Example 16 illustrates and discusses the necessary reaction conditions. Although other zinc (II) salts might be used (e.g. $ZnSO_4$), $ZnCl_2$ is preferred because the HCl byproduct it produces is volatile.

R groups in which X is 4-phenylene are preferred because the para-linkage permit freer rotation of the sulfonyl chain and thus provides greater thermal stability. Similarly, R groups containing only two benzene rings (i.e. Y represents a direct bond) are preferred because they have greater thermal stability than R groups containing 3 benzene rings. Thus, 4-(phenylsulfonyl)phenyl is the most preferred R group.

The unsymmtic phosphinic acids of this invention (i.e., R' is lower alkyl of from 1 to 3 carbon atoms, 4-biphenylyl or phenyl) are preferred because they produce polymers which are easier to melt and/or solution process than do the symetric phosphinic acids (i.e., R' = R). R' is limited to alkyl of up to 3 carbon atoms because polymers containing larger alkyl groups do not have sufficient thermal stability. Methyl is the preferred alkyl group because it is more thermally stable than the ethyl and propyl groups. Similarly, phosphinic acids in which R' is phenyl produce polymers with greater thermal stability than do phosphinic acids in which R' is 4-(biphenylyl).

Dimethyl formamide appears to be the best solvent for applying the polymer coatings; it dissolves sulfonyl containing compounds or polymers better than most solvents and it is acceptable for use in paints. Although chloroform will dissolve many of these polymers, it is unsuitable for coatings such as paints because it is volatile and poisonous.

Even if a polymer is not solution or melt processable, a suitable coating can frequently be obtained by dissolving the phosphinic acid and $ZnCl_2$ together and then spraying the solution onto the surface to be coated. The solvent is allowed to evaporate and the resulting polymer coating is cured.

The general nature of the invention having been set forth, the following examples are presented as specific illustrations thereof. It will be understood that the invention is not limited to these specific examples but is susceptible to various modifications that will be recognized by one of ordinary skill in the art.

EXAMPLE I bis [4-(phenylsulfonyl)phenyl] phosphinic acid

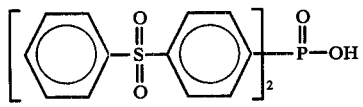

A solution of 30 grams (0.1 mole) of 4-bromophenyl phenyl sulfone in 500 ml. of tetrahydrofuran was cooled to −100° C. in a liquid nitrogen-toluene slush, and 42 ml. (0.1 mole) of 2.38 M n-butyl lithium in hexane was added, forming 4-phenylsulfonyl-phenyl lithium. After about 10 minutes, 9.5 grams (0.05 mole) of diethyl dichlorophosphoramide was added, and the reaction mixture was allowed to warm slowly to room temperature, and then to stand a room temperature for 18 hours, forming diethyl bis [4-(phenylsulfonyl)phenyl] phosphoramide. Next, 125 ml. of 6 M HCl was added, and the reaction mixture was heated under reflux for 4 hours to hydrolyze the phosphoramide group. The tetrahydrofuran was removed by distillation, and 7.5 grams of almost white solid, M.P. 115°–130° C., was collected by filtration. This solid was recrystallized from tetrahydrofuran to give 7 grams (28% yield) of the bis[4-(phenylsulfonyl)phenyl] phosphinic acid product, m.p. 155°–165° C.

Analysis. Calculated for $C_{24}H_{19}O_6PS_2$ (weight percent):
C, 57.8; H, 3.84; P, 6.21; S, 12.86.
Found: C, 58.5; H, 4.55; P, 6.02; S, 13.06.

This reaction was repeated using a greater ratio of the bromide to diethyl dichlorophosphoramide without significant increase in yield.

EXAMPLE 2

4-bromophenyl 4-(phenylsulfonyl)phenyl ether

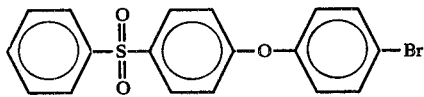

To a mixture of 22.4 grams of powdered potassium hydroxide and 94 grams of 4-(phenylsulfonyl)phenol in 100 ml. of dimethylformamide were added while stirring under nitrogen, 400 grams of 4-dibromobenzene and 2 grams of precipitated copper. The reaction mixture was heated at 190°±5° C. for 16 hours, and excess dibromobenzene was then removed by distillation. The pot residue was dissolved in 500 ml. of benzene and washed with 10% aqueous potassium hydroxide and water. The benzene was removed under reduced pressure, and the residue was dissolved in 4 liters of ether. A small amount of insoluble material was removed by filtration, and 68 grams of 4-bromophenyl 4-(phenylsulfonyl)phenyl ether, m.p. 114°–117° C. was precipitated by adding methanol while the ether was boiled off.

Analysis. Calculated for $C_{18}H_{13}BrO_3S$ (weight percent): C, 55.53; H, 3.37; Br, 20.54; Found: C, 55.72; H, 3.50; Br, 20.63.

EXAMPLE 3 bis{4-[4-(phenylsulfonyl)phenoxy]phenyl} phosphinic acid

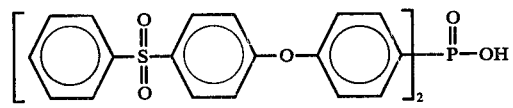

The procedure given in example 1 was used to convert 30 grams of 4-bromophenyl 4-(phenylsulfonyl)phenyl ether (produced in example 2) to 14 grams of bis{4-[4-(phenylsulfonyl)phenoxy]phenyl} phosphinic acid, m.p. 225°–230° C.

Analysis. Calculated for $C_{36}H_{27}O_8PS_2$ (weight percent): C, 63.33; H, 4.00; P, 4.53. Found: C, 61.40; H, 4.05; P, 4.92.

EXAMPLE 4 methyl[4-(phenylsulfonyl)phenyl]phosphinic acid

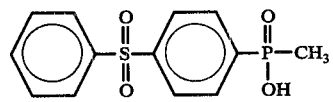

The procedure given in example 1 was used to convert 29.7 grams of 4-bromophenyl phenyl sulfone and 18.7 grams of diethyl chloromethylphosphoramide to 3 grams of methyl[4-(phenylsulfonyl)phenyl]phosphinic acid, m.p. 73°–76° C.

Analysis. Calculated for $C_{13}H_{13}O_4PS$ (weight percent): C, 52.71; H, 4.43; P, 10.43. Found. C, 50.50; H, 4.82; P, 10.59.

EXAMPLE 5

4-(Dimethylthiocarbamoyloxy)phenyl phenyl sulfone

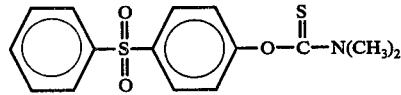

To a slurry of 190 grams (0.81 mole) of 4-(phenylsulfonyl)-phenol in a solution of 32 grams (0.81 mole) of sodium hydroxide in 2 liters of water was added slowly with stirring a solution of 112 grams (0.9 mole) of dimethylthiocarbamoyl chloride in 800 ml. of ether while the temperature of the reaction was maintained in the 0°–10° C range with external cooling. After the addition was complete, the basicity of the solution was adjusted to pH 8 by addition of dilute sodium hydroxide. The reaction mixture was stirred at room temperature for 2 hours, and 187.5 grams (72% yield) of crude product, m.p. 91°–110° C was then collected. After the analytical sample was recrystallized from ethanol, it melted at 134°–135.5° C.

Analysis. Calculated for $C_{15}H_{15}NO_3S_2$ (weight percent): C, 56.1; H, 4.70. Found: C, 56.0; H, 5.02.

EXAMPLE 6

4-(Dimethylcarbamoylthio)phenyl phenyl sulfone

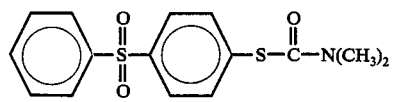

Heating of the crude solid product of example 5 for 3 hours at 160° C with subsequent crystallization from ethanol gave 18 grams of crude product, m.p. 107°–111° C. An analytical sample, which was recrystallized from ethanol, melted at 121°–125° C.

Analysis. Calculated for $C_{15}H_{15}NO_3S_2$ (weight percent): C, 56.1; H, 4.70. Found: C, 55.9; H, 4.79.

Confirmation of the rearrangment was obtained from the appearance of an amide CO band at 1640 cm$^{-1}$ in the ir.

EXAMPLE 7

4-(phenylsulfonyl)thiophenol

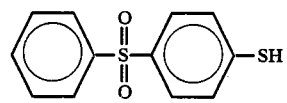

The 4-(dimethylcarbamoylthio)phenyl phenyl sulfone formed in Example 6 was hydrolyzed by refluxing it in dilute KOH in water for about 1 to 2 hours. The concentration of the KOH was not critical. The product formed was 4-(phenylsulfonyl)thiophenol.

EXAMPLE 8

4-nitrophenyl 4-(phenylsulfonyl)phenyl sulfide

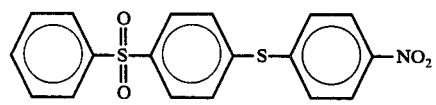

Sodium metal was added to ethanol to form sodium ethoxide, $CH_3CH_2ONa$. Next the 4-(phenylsulfonyl)thiophenol formed in Example 8 was added to the sodium ethoxide, forming the sodium salt of the thiophenol,

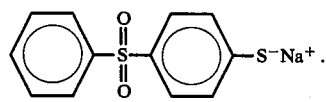

Finally, the 4-chloronitrobenzene was added and the mixture was refluxed for 3 hours, forming the 4-nitrophenyl 4-(phenylsulfonyl) phenyl sulfide.

EXAMPLE 9

4-(4-nitrophenylsulfonyl)phenyl phenyl sulfone

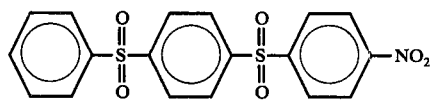

A solution of 8.1 grams (0.05 mole) of potassium permanganate in 150 ml of water was added slowly to a solution of 14 grams (0.038 mole) of the 4-nitrophenyl4-(phenylsulfonyl)phenyl sulfide produced in example 9 in 250 ml. of acetic acid. The resulting mixture was stirred for 1.5 hours, warmed on a steam bath for another 1.5 hours, and then the excess manganese dioxide was decomposed with sodium bisulfite. The reaction mixture was then cooled with an equal volume of ice, and 14.2 grams (88% yield) of product, m.p. 289°–298° C, was collected by filtration.

Analysis. Calculated for $C_{18}H_{13}NO_6S_2$ (weight percent): C, 53.6; H, 3.25; N, 3.47. Found: C, 53.4; H, 3.35; N, 3.68.

EXAMPLE 10

4-(4-aminophenylsulfonyl)phenyl phenyl sulfone

A warm slurry of 13.5 grams (0.034 mole) of the 4-(4-nitrophenylsufonyl)phenyl phenyl sulfone of example 9 in 450 ml. of dimethylformamide was hydrogenated at an initial hydrogen pressure of 60 psi and in the present of 10 ml. of slurry of Raney nickel in ethanol. The theoretical amount of hydrogen was consumed in 6 hours. The catalyst was removed by filtration, and the filtrate was concentrated to dryness. The residue was crystallized in 50 ml. of ethanol to give 10 grams (79% yield) of product, m.p. 231°–5° C. An analytical sample was recrystallized from ethanol to give material melting at 234.5°–237° C.

Analysis. Calculated for $C_{18}H_{15}NO_4S_2$ (weight percent); C, 57.9; H, 4.06; N, 3.75. Found: C, 57.8; H, 4.29, N, 3.82.

EXAMPLE 11

4-[4-(phenylsulfonyl)phenylsulfonyl]benzenediazonium tetrafluoroborate

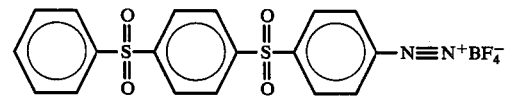

To a slurry of 10 grams (0.027 mole) of finely ground 4-(4-aminophenylsulfonyl)phenyl phenyl sulfone (prepared in example 9) in 200 ml. of tetrafluoroboric acid solution was added slowly 5 grams (0.073 mole) of sodium nitrite in 10 ml. of water, with cooling to 0°–10° C. The resulting solid was collected by filtration, washed with 10 ml. of cold aqueous tetrafluoroboric acid, then 10 ml of ethanol, and finely 50 ml of ether, and dried. Yield of 4-[4-(phenylsulfonyl)phenylsulfonyl]benzenediazonium tetrafluoroborate 11 grams (95%), m.p. 120°–130° C.

The solution of tetrafluoroboric acid used in these examples was prepared by dissolving 184 grams of boric acid in 454 grams of 48% hydrofluoric acid.

EXAMPLE 12

Phenyl{4-[4-(phenylsulfonyl)phenylsulfonyl]-phenyl}phosphinic acid

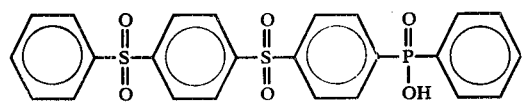

A slurry of 11 grams (0.026 mole) of the 4-[4-(phenylsulfonyl)phenylsulfonyl]benzenediazonium tetrafluoroborate prepared in Example 11, 0.01 grams of copper (I) bromide, and 5 ml. (0.06 mole) of dichlorophenylphosphine in 100 ml. of ethyl acetate was warmed at 40°–50° for 30 minutes. The resulting solution was cooled, and 200 ml. of water was added. Ethyl acetate and volatile by-products were removed by steam distillation, and the crude product was collected by filtration. This solid was partially dissolved in 500 ml. of 5% potassium carbonate and reprecipitated with hydrochloric acid to give 3.1 grams of solid, m.p. 125°–150°. Recrystallation from 200 ml. of ethanol gave 2 grams (15% yield) of the phenyl{4-[4-(phenylsulfonyl)phenylsulfonyl]phenyl}-phosphinic acid, m.p. 227–230.

Analysis. Calculated for $C_{24}H_{19}O_6PS_2$ (weight percent): C, 57.8; H, 3–84; P, 6.21; S, 12.86. Found: C, 57.6: H, 4.04; P, 6.17; S, 12.80.

EXAMPLE 13 phenyl[4-(phenylsulfonyl)phenyl]phosphinic acid

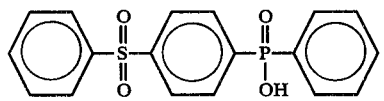

4-(phenylsulfonyl)benzene diazonium tetrafluoroborate was prepared from 4-aminophenyl phenyl sulfone according to the method of example 11. A slurry of 44 grams of the 4-(phenylsulfonyl)benzenediazonium tetrafluoroborate, 22.8 ml of dichlorophenylphosphine, and 0.5 grams of copper (I) chloride in 400 ml. of ethyl acetate was heated at 30° C for 1.5 hours, cooled, and decomposed by adding 125 ml. of water. The ethyl acetate was removed by steam distillation, and the solid was collected by filtration of the aqueous residue. This solid was extracted with 2 liter of 10% sodium hydroxide, and the extract was acidified with hydrochloric acid to give crude acid. Crystallization from 80% ethanol gave 20 grams (45% yield) of phenyl[4-(phenylsulfonyl)phenyl]phosphinic acid, m.p. 225°–228° C.

Analysis. Calculated for $C_{18}H_{15}O_4PS$ (weight percent): C, 60.3; H, 4.23; P, 8.64; S, 8.95. Found: C, 60.2; H, 4.49; P, 8.77; S, 9.49.

EXAMPLE 14 phenyl[3-(phenylsulfonyl)phenyl]phosphinic acid

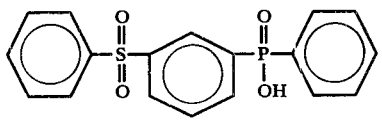

3-(phenylsulfonyl)benzene diazonium tetrafluoroborate was prepare from 3-aminophenyl phenyl sulfonate according to the method of example 11. 14.3 grams of the 3-(phenylsulfonyl)benzene diazonium tetrafluoroborate was reacted with 20 grams of dichlorophenyl phosphine according to the procedure of example 13 and gave 6.1 grams (39.5% yield) of phenyl [3-(phenylsulfonyl)phenyl]phosphinic acid, m.p. 175°–177° C.

Analysis. Calculated for $C_{18}H_{15}O_4PS$ (weight percent): C, 60.3; H, 4.23; P, 8.64. Found: C, 60.3; H, 4.52; P, 8.47.

EXAMPLE 15

4-(biphenylyl) [4-(phenylsulfonyl)phenyl]phosphinic acid hydrate

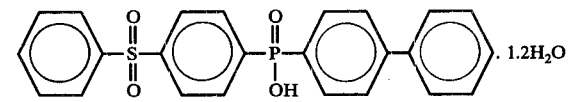

The reaction of 18.9 grams of 4-(phenylsulfonyl)benzene diazonium tetrafluroborate with 15.7 grams of 4-biphenylyldichlorophosphine according to the procedure of example 13 gave 9 grams of 4-(biphenylyl) [4-(phenylsulfonyl)phenyl]-phosphinic acid hydrate, m.p. 179°–230° C.

Analysis. Calculated for $C_{24}H_{19}O_4PS \cdot 1.2H_2O$ weight percent: C, 63.21; H, 4.74; S, 7.03. Found: C, 63.04; H, 4.52; S, 6.73.

EXAMPLE 16

Synthesis of Zinc Phosphinates

All of the zinc bis(phosphinates) were synthesized by the same general procedure. The phosphinic acid (or acids for the copolymer) was first neutralized with $K_2CO_3$ in a tetrahydrofuran/water mixture by treating it with the stoichiometric amount of $K_2CO_3$ (0.5 mole per mole of acid). An excess of $K_2CO_3$ was avoided, so that zinc hydroxy phosphinates would not be formed in the next step. The potassium phosphinate solution was then added slowly with stirring to an aqueous solution of zinc sulfate (0.5 mole of zinc sulfate per mole of potassium phosphinate). After the addition was completed, the solution was heated to and held at boiling until all the tetrahydrofuran was removed. The precipitate that formed was filtered off, washed with water, and dried in a vacuum desiccator. Yields were 85% or better. Table I gives analytical and softening point data for five of the zinc bis(phosphinates) prepared and molecular weights for the two polymers that are soluble in chloroform. The thermal stabilities of the various zinc phosphinates were measured in both nitrogen and air, and the results are given in Table II.

Table I
Summary of Analytical Data for Zinc Phosphinate Polymers and Copolymers

| | Analysis (%) a | | | Softening Point (° C) | Molecular weight b in CHCl₃ |
|---|---|---|---|---|---|
| | C | H | Zn | | |
| 1. Zn[OP((⌬)—SO₂—(⌬))₂O]₂ | 54.0 (54.4 | 3.42 3.42 | 6.16 6.08) | >400 | c |
| 2. Zn[OP ((⌬)) ((⌬)—SO₂—(⌬))O]₂ | 55.0 (55.4 | 4.00 3.62 | 7.98 8.38) | 180 | c |
| 3. Zn[OP ((⌬)) ((⌬)—SO₂—(⌬)—SO₂—(⌬))O]₂ | 54.1 (54.4 | 4.06 3.42 | 5.72 6.16) | 400 | c |
| 4. Zn[OP ((⌬)) ((⌬))O]₂ with SO₂-(⌬) | 55.7 (55.4 | 4.03 3.62 | 8.40 8.38) | 140 | 20,000 (8,000) |
| 5. Zn[OP ((⌬)) ((⌬)—SO₂—(⌬))O] [OP ((⌬)) ((⌬))O] with SO₂-(⌬) | 55.4 (55.4 | 3.94 3.62 | 7.93 8.38) | 155 | 28,000 (15,000) | a Calculated values in parentheses.
b Values in parenthesis are for unpurified CHCl₃ (0.75% C₂H₅OH). Values are ±5%.
c Insoluble in chloroform.

Table II
Thermogravimetric Analyses of Zinc Phosphinate Polymers and Copolymers

| | | Temp. (°C) for Indicated Wt. Loss b | | | |
|---|---|---|---|---|---|
| Polymer | Atmos.a | Initial | 2% | 5% | 10% |
| 1. | N | 440 | 450 | 485 | 495 |
| | A | 440 | 450 | 480 | 500 |
| 2. | N | 440 | 450 | 465 | 475 |
| | A | 450 | 460 | 495 | 500 |
| 3. | N | 385 | 400 | 440 | 460 |
| | A | 350 | 400 | 450 | 470 |
| 4. | N | 410 | 415 | 440 | 455 |
| | A | 355 | 400 | 440 | 455 |
| 5. | A | 365 | 400 | 450 | 460 | aThe atmosphere during the run was nitrogen (N) or air (A).
bHeating rate 5°/min.

With the exception of polymer number 3, these zinc (II) bis(phosphinate) polymers are soluble in organic solvents such as dimethylformamide tetrahydrofuran and/or chloroform.

Obviously, numerous modification and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A phosphinic acid of the formula $$R-\overset{\overset{O}{\|}}{\underset{OH}{P}}-R'$$

wherein
(a) R has the formula

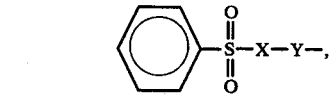

(1) x is select from the group consisting of 3-phenylene and 4-phenylene, and
(2) y is select from the group consisting of a direct bond,

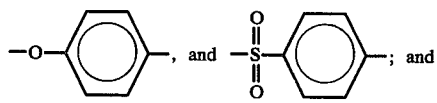

(b) R' is selected from the group consisting of R, lower alkyl of from 1 to 3 carbon atoms, 4-biphenylyl, and phenyl.

2. A phosphinic acid according to claim 1 wherein R' is identical to R.

3. A phosphinic acid according to claim 2 wherein y is a direct bond.

4. A phosphinic acid according to claim 3 having the formula

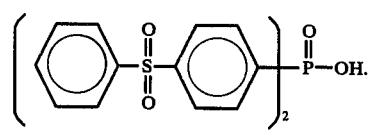

5. A phosphinic acid according to claim 2 wherein y is

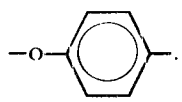

6. A phosphinic acid according to claim 5 having the formula

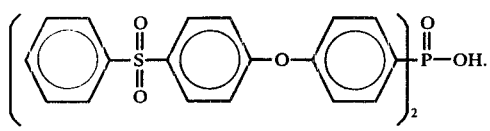

7. A phosphinic acid according to claim 2 wherein y is

8. A phosphinic acid according to claim 7 having the formula

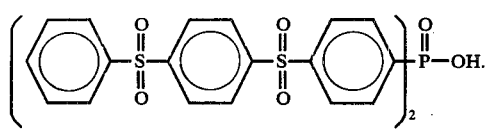

9. A phosphinic acid according to claim 1 wherein R' is a lower alkyl of from 1 to 3 carbon atoms.

10. A phosphinic acid according to claim 9 wherein y is a direct bond.

11. A phosphinic acid according to claim 10 wherein x is 4-phenylene.

12. A phosphinic acid according to claim 10 wherein R' is methyl.

13. A phosphinic acid according to claim 12 having the formula

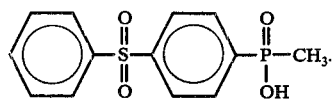

14. A phosphinic acid according to claim 9 wherein y is

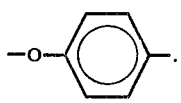

15. A phosphinic acid according to claim 14 wherein x is 4-phenylene.

16. A phosphinic acid according to claim 14 wherein R' is methyl.

17. A phosphinic acid according to claim 16 having the formula

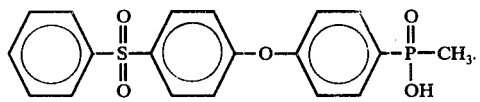

18. A phosphinic acid according to claim 9 wherein y is

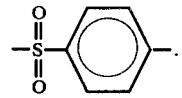

19. A phosphinic acid according to claim 18 wherein x is 4-phenylene.

20. A phosphinic acid according to claim 18 wherein R' is methyl.

21. A phosphinic acid according to claim 20 having the formula

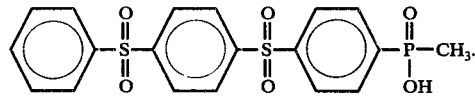

22. A phosphinic acid according to claim 1 wherein R' is selected from the group consisting of 4-biphenylyl and phenyl.

23. A phosphinic acid according to claim 22 wherein y is a direct bond.

24. A phosphinic acid according to claim 23 wherein x is 4-phenylene.

25. A phosphinic acid according to claim 23 wherein R' is phenyl.

26. A phosphinic acid according to claim 25 having the formula

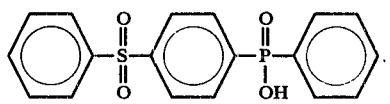

27. A phosphinic acid according to claim 22 wherein y is

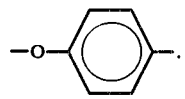

28. A phosphinic acid according to claim 27 wherein x is 4-phenylene.

29. A phosphinic acid according to claim 27 wherein R' is phenyl.

30. A phosphinic acid according to claim 29 having the formula

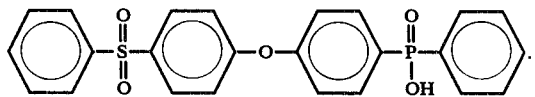

31. A phosphinic acid according to claim 22 wherein y is

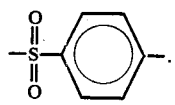

32. A phosphinic acid according to claim 31 wherein x is 4-phenylene.

33. A phosphinic acid according to claim 31 wherein R' is phenyl.

34. The phosphinic acid of claim 33 having the formula

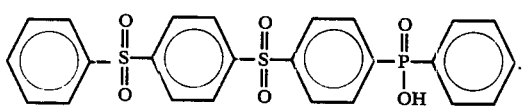

35. An alkali metal salt of a phosphinic acid of the formula

wherein
(a) R has the formula

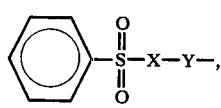

(1) x is selected from the group consisting of 3-phenylene and 4-phenylene, and
(2) y is selected from the group consisting of a direct bond,

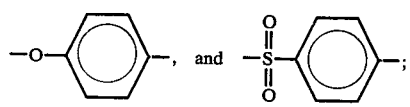

(b) R' is selected from the group consisting of R, lower alkyl of from 1 to 3 carbon atoms, 4-biphenylyl and phenyl; and
(c) M is an alkali metal.

36. An alkali metal salt according to claim 35 wherein R' is identical to R.

37. An alkali metal salt according to claim 36 wherein y is a direct bond.

38. An alkali metal salt according to claim 37 wherein x is 4-phenylene.

39. An alkali metal salt according to claim 36 wherein y is

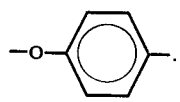

40. An alkali metal salt according to claim 39 wherein x is 4-phenylene.

41. An alkali metal salt according to claim 36 wherein y is

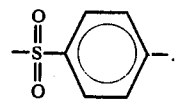

42. An alkali metal salt according to claim 41 wherein x is 4-phenylene.

43. An alkali metal salt according to claim 35 wherein R' is a lower alkyl of from 1 to 3 carbon atoms.

44. An alkali metal salt according to claim 43 wherein y is a direct bond.

45. An alkali metal salt according to claim 44 wherein x is 4-phenylene.

46. An alkali metal salt according to claim 44 wherein R' is methyl.

47. An alkali metal salt according to claim 46 wherein x is 4-phenylene.

48. An alkali metal salt according to claim 43 wherein y is

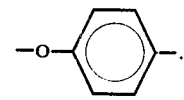

49. An alkali metal salt according to claim 48 wherein x is 4-phenylene.

50. An alkali metal salt according to claim 48 wherein R' is methyl.

51. An alkali metal salt according to claim 50 wherein x is 4-phenylene.

52. An alkali metal salt according to claim 43 wherein y is

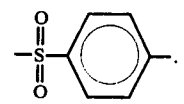

53. An alkali metal salt according to claim 52 wherein x is 4-phenylene.

54. An alkali metal salt according to claim 52 wherein R' is methyl.

55. An alkali metal salt according to claim 54 wherein x is 4-phenylene.

56. An alkali metal salt according to claim 35 wherein R' is selected from the group consisting of 4-biphenylyl and phenyl.

57. An alkali metal salt according to claim 56 wherein y is a direct bond.

58. An alkali metal salt according to claim 57 wherein x is 4-phenylene.

59. An alkali metal salt according to claim 57 wherein R' is phenyl.

60. An alkali metal salt according to claim 59 wherein x is 4-phenylene.

61. An alkali metal salt according to claim 56 wherein y is

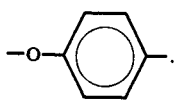

62. An alkali metal salt according to claim 61 wherein x is 4-phenylene.

63. An alkali metal salt according to claim 61 wherein R' is phenyl.

64. An alkali metal salt according to claim 62 wherein x is 4-phenylene.

65. An alkali metal salt according to claim 56 wherein y is

66. An alkali metal salt according to claim 65 wherein x is 4-phenylene.

67. An alkali metal salt according to claim 65 wherein R' is phenyl.

68. An alkali metal salt according to claim 67 wherein x is 4-phenylene.

* * * * *